United States Patent
Clegg et al.

(10) Patent No.: US 9,458,428 B2
(45) Date of Patent: Oct. 4, 2016

(54) METHODS AND COMPOSITIONS FOR THE RAPID PRODUCTION OF RETINAL PIGMENTED EPITHELIAL CELLS FROM PLURIPOTENT CELLS

(71) Applicant: The Regents of the University of California, Oakland, CA (US)

(72) Inventors: Dennis Clegg, Ventura, CA (US); David Buchholz, New York, NY (US); Roxanne Croze, Santa Barbara, CA (US); Britney Pennington, Santa Barbara, CA (US); Peter Coffey, Bedfordshire (GB); Lyndsay Leach, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 7 days.

(21) Appl. No.: 14/405,730

(22) PCT Filed: Jun. 5, 2013

(86) PCT No.: PCT/US2013/044325
§ 371 (c)(1),
(2) Date: Dec. 4, 2014

(87) PCT Pub. No.: WO2013/184809
PCT Pub. Date: Dec. 12, 2013

(65) Prior Publication Data
US 2015/0175964 A1 Jun. 25, 2015

Related U.S. Application Data
(60) Provisional application No. 61/655,977, filed on Jun. 5, 2012.

(51) Int. Cl.
C12N 5/00 (2006.01)
C12N 5/02 (2006.01)
C12N 5/071 (2010.01)
C12N 5/079 (2010.01)

(52) U.S. Cl.
CPC .......... *C12N 5/0621* (2013.01); *C12N 2500/05* (2013.01); *C12N 2500/30* (2013.01); *C12N 2500/36* (2013.01); *C12N 2500/38* (2013.01); *C12N 2501/105* (2013.01); *C12N 2501/113* (2013.01); *C12N 2501/115* (2013.01); *C12N 2501/155* (2013.01); *C12N 2501/16* (2013.01); *C12N 2501/33* (2013.01); *C12N 2501/35* (2013.01); *C12N 2501/392* (2013.01); *C12N 2501/395* (2013.01); *C12N 2501/40* (2013.01); *C12N 2501/415* (2013.01); *C12N 2501/727* (2013.01); *C12N 2501/998* (2013.01); *C12N 2506/02* (2013.01)

(58) Field of Classification Search
CPC .................................................... C12N 5/0621
USPC .......................................................... 435/377
See application file for complete search history.

(56) References Cited

U.S. PATENT DOCUMENTS

2007/0196919 A1 8/2007 Reh et al.
2011/0097799 A1 4/2011 Stankewicz et al.
2012/0101024 A1 4/2012 Stern et al.

FOREIGN PATENT DOCUMENTS

WO 9506112 A1 3/1995
WO 2009147400 A1 12/2009
WO 2011149762 A2 12/2011

*Primary Examiner* — Valarie Bertoglio
(74) *Attorney, Agent, or Firm* — Mountain IP

(57) ABSTRACT

The invention relates to the field of cell culture, specifically, the derivation of retinal pigmented epithelial cells from pluripotent cells. The invention comprises the use of various cell culture medium supplements, medium formulations, and methods of using such medium supplements and formulations, in order to effect the rapid differentiation of pluripotent cells into retinal pigmented epithelial cells with very high yields. The invention further includes cell culture media formulations for the efficient maintenance, propagation, and maturation of cultured retinal pigmented epithelial cells.

10 Claims, No Drawings

METHODS AND COMPOSITIONS FOR THE RAPID PRODUCTION OF RETINAL PIGMENTED EPITHELIAL CELLS FROM PLURIPOTENT CELLS

CROSS-REFERENCE TO RELATED APPLICATIONS

This application is based on and claims the benefit of priority of U.S. Provisional Patent Application Ser. No. 61/655,977 filed on Jun. 5, 2012, the contents of which are incorporated by reference, and PCT Application Serial Number PCT/US2013/044325, filed Jun. 5, 2013, the contents of which are incorporated by reference.

STATEMENT REGARDING FEDERALLY SPONSORED RESEARCH OF DEVELOPMENT

This invention was made with government support under Grant # W911NF-09-0001 awarded by the U.S. Army Research Office. The government has certain rights in the invention.

REFERENCE TO SEQUENCE LISTING, A TABLE, OR A COMPUTER PROGRAM LISTING COMPACT DISK APPENDIX

Not Applicable

FIELD OF THE INVENTION

The invention relates to the field of cell culture, specifically the culturing of retinal pigmented epithelium (RPE) cells. The invention encompasses methods and compositions for the rapid and efficient production of RPE cells from pluripotent cells. The invention further includes methods and compositions for the efficient expansion, maintenance, and culture of differentiated RPE cells from native and pluripotent cell sources.

BACKGROUND OF THE INVENTION

The retinal pigmented epithelium (RPE) is a layer of cells in the eye. The RPE is overlaid by the sensory retina cells which perceive light and transmit visual information to the optic nerve. Underlying the RPE is the choroid tissue, a vascularized region which supplies the overlying cells of the eye with water, nutrients and other compounds. The RPE plays many critical roles in maintaining vision including isolating the tissues of the eye from the general circulatory system, maintaining the proper ionic environment, processing discarded outer photoreceptor elements from the photoreceptor cells of the neural retina, and protecting the retina from excess light. RPE cells form a flat mosaic of hexagonal cells tightly bound at their junctions.

Various conditions may result in damage and dysfunction of the RPE cells. For example, in some forms of retinitis pigmentosa, RPE cells exhibit abnormalities and dysfunction that affect vision. Another example is age-related macular degeneration (AMD), a disease that gradually diminishes vision in the macula, or central region of the eye. AMD is a leading cause of vision loss in persons 60 years of age and older. It is estimated that in the United States 30% of people over age 75 suffer from some form of AMD. There are few therapies available for AMD and none that effectively cure or reverse the condition. In some forms of AMD, deposits of cellular debris (drusen) form between the RPE and the underlying nourishing choroid, leading to death and dysfunction of the RPE cells. Choroidal neovascularization (CNV) is an AMD subtype characterized by abnormal blood vessel proliferation of the choroidal tissue and the resultant loss of vision resulting from damage to the overlying retinal cells. Geographic atrophy is another form of AMD characterized by atrophy of the retinal pigmented epithelial cells and the resultant death of the overlying retinal cells.

It has been demonstrated, both in animal tests and in human trials, that transplantation of healthy RPE cells to damaged or destroyed regions of the retina can aid in restoring vision (da Cruz et al., RPE transplantation and its role in retinal disease, Progress in Retinal and Eye Research 26:598-635 (2007)). For example, in patients with CNV, surgery to remove the heavily vascularized tissue followed by transplant of RPE cells from the patients' own eyes was shown to restore vision (Chen, et al., Long-term visual and microperimetry outcomes following autologous retinal pigment epithelium choroid graft for neovascular age-related macular degeneration, Clinical and Experimental Ophthamology 37:275-285 (2009)).

To maximize therapeutic potential, it would be advantageous to obtain large supplies of immune-compatible RPE cells for transplant purposes. RPE cells derived from stem cells and induced pluripotent cells present such a potential source of abundant RPE tissues for transplant. For example, RPE cells derived from both human embryonic and induced pluripotent stem cells have been created and transplanted in rats and were shown to be functional (Carr et al., Protective Effects of Human iPS-Derived Retinal Pigment Epithelium Cell Transplantation in the Retinal Dystrophic Rat, PloS One 4(12):e8152 (2009)). RPE cells from human embryonic stem cells are currently in clinical trials for the treatment of both AMD and Stargardt's macular dystrophy.

The derivation of RPE cells from pluripotent cells has been demonstrated previously, for example, as described in Buchholz et al., Derivation of Functional Retinal Pigmented Epithelium from Induced Pluripotent Stem Cells, Stem Cells 27:2427-2434 (2009), and in Can et al., Molecular Characterization and functional analysis of phagocytosis by human embryonic stem cell-derived RPE cells using a novel human retinal assay, Mol Vis 15:283-295 (2009). However, the known protocols for deriving RPE from pluripotent cells are inefficient, typically giving rise to 1-5% differentiated RPE cells. Only one group has reported substantially higher yields, reporting a yield of 33% differentiated RPE cells (Idelson, M., R. Alper, et al. (2009). "Directed differentiation of human embryonic stem cells into functional retinal pigment epithelium cells." *Cell Stem Cell* 5(4): 396-408). In addition to the low yields of the prior art methods, these methods require many months for the production of functional RPE cells in usable quantities. Accordingly, there is a need in the art for facile, high yielding and highly consistent methods of creating viable RPE cells from pluripotent cells.

SUMMARY OF THE INVENTION

Disclosed herein are novel methods and compositions for producing high-quality RPE cells with very high yields (>80%). Additionally, the novel protocol disclosed herein is extremely fast, and usable quantities of cells may be produced in as little as two weeks. Also disclosed herein are methods and compositions for the efficient maturation, maintenance, and expansion of differentiated RPE cells. The inventions described herein encompass the use of novel media formulations, encompassing a range of constituents and which may be applied in a specific sequence and with specific timing for the rapid differentiation of RPE cells from pluripotent cells. Additionally, the use of novel media compositions, and media supplementation with ROCK inhibitors in the maturation, maintenance, and expansion of differentiated RPE cells is described. In one aspect, the invention comprises novel media formulations for the differentiation of RPE cells from pluripotent cells. In another aspect, the invention comprises the supplementation of known media compositions with compositions that aid in the rapid and efficient differentiation of RPE cells from pluripotent cells. In another aspect, the invention comprises methods of culturing pluripotent and differentiating cells in various media compositions for the rapid differentiation and maturation of such cultured cells into functional RPE cells. In another aspect, the invention comprises kits which are made up of multiple media formulations, or media multiple supplements which may be added to a basal medium to create one of the media of the invention. In another aspect, the invention comprises the use of ROCK inhibitors in culture media during various phases of the differentiation, maintenance, and expansion of RPE cell cultures.

DETAILED DESCRIPTION OF THE INVENTION

RPE from Pluripotent Cells. The invention provides novel methods of producing RPE cells from pluripotent cells utilizing a variety of media, the media being used in a sequence and timing which promotes very rapid differentiation of RPE cells. Some of the media constituents utilized in the media of the invention are known in the differentiation of RPE cells. For example, nicotinamide is known to promote differentiation of RPE from pluripotent cells (as described in Idelson M, Alper R, Obolensky A et al. Directed differentiation of human embryonic stem cells into functional retinal pigment epithelium cells. Cell Stem Cell 2009; 5:396-408). Likewise, VIP has previously been used in the production of RPE cells (Koh S M. VIP enhances the differentiation of retinal pigment epithelium in culture: From cAMP and pp60(c-src) to melanogenesis and development of fluid transport capacity. Prog Retin Eye Res 2000; 19:669-688). However, the combinations of media constituents disclosed herein, and the timing of their application, results in the production of RPE with unprecedented speed and efficiency. Drawing upon knowledge from developmental biology, retinal progenitor development, and other stem cell studies, the timing of factor addition has been optimized to generate high-quality RPE within 14 days, with high yields.

For purposes of this disclosure, the term "RPE cells" refers to native pigmented retinal epithelial cells as well as pigmented retinal epithelial phenotype cells derived from pluripotent cell sources. Such cultured cells have a genetic expression profile similar to that of native RPE cells and assume the polygonal, planar sheet morphology of native RPE cells when grown to confluence on a planar substrate.

For purposes of this disclosure, the term "pluripotent cells" refers to cells that can self-renew and proliferate while remaining in an undifferentiated state and that can, under the proper conditions, be induced to differentiate into specialized cell types, including RPE cells. The term "pluripotent cells," as used herein, encompass embryonic stem cells and other types of stem cells, including fetal, amnionic, or somatic stem cells. Exemplary human stem cell lines include the H9 human embryonic stem cell line. Additional exemplary stem cell lines include those made available through the National Institutes of Health Human Embryonic Stem Cell Registry and the Howard Hughes Medical Institute HUES collection (as described in Cowan, C. A. et. al, Derivation of Embryonic Stem-cell Lines from Human Blastocysts. New England Journal of Medicine. 350; 13. (2004)). The term "pluripotent cells," as used herein, also encompasses induced pluripotent stem cells, a type of pluripotent stem cell which has been derived from a non-pluripotent cell, such as a somatic cell that has been reprogrammed to induce a pluripotent, undifferentiated phenotype by various means. iPS cells can be created by inducing the expression of certain regulatory genes or by the exogenous application of certain proteins. Methods for the induction of iPS cells are known in the art and include, for example, the methods described in Zhou et al., Adenoviral gene delivery can reprogram human fibroblasts to induced pluripotent stem cells, *Stem Cells* 27 (11): 2667-74 (2009), Huangfu et al., Induction of pluripotent stem cells by defined factors is greatly improved by small-molecule compounds, *Nature Biotechnology* 26 (7): 795 (2008); Woltjen et al., piggyBac transposition reprograms fibroblasts to induced pluripotent stem cells, *Nature* 458 (7239): 766-770 (2009); Zhou et al., Generation of Induced Pluripotent Stem Cells Using Recombinant Proteins, Cell Stem Cell 8:381-384 (2009).

The invention encompasses the use of pluripotent cells from any species, including human, murine, porcine, canine, feline, rattus, and other mammal species. Cells derived through the use of the invention may be applied in any research or therapeutic use, including medical and veterinary uses.

Pluripotent cells can be cultured and differentiated to RPE using various culture methods and conditions known in the art. Pluripotent cells may be grown in any type of suitable vessel including vessels made from glass, polystyrene, and polycarbonate. The invention encompasses the use of any cell culture system, including 2-dimensional culture, three-dimensional culture, and liquid suspension culture techniques. Two-dimensional culture techniques are preferred for the ease of cell observation and passaging. Vessels of any size may be used, such as T-75 flasks (75 $cm^2$ surface area/flask), 96-well plates (0.32 $cm^2$ surface area/well), 24-well plates (1.9 $cm^2$ surface area/well), or six well plates (9.5 $cm^2$ surface area/well), for example BD Falcon™ polystyrene plates. Cell cultures should be maintained at or near 37° C. Adequate medium to avoid limiting growth should be added to each vessel, and medium should be changed at regular intervals to avoid depletion of nutrients and accumulation of waste substances. For example, using standard six-well plates (well diameter of 9.5 $cm^2$), about 2 ml of medium should be used per well.

Substrates

In preferred embodiments, the cell culture methods of the invention are carried out using a cell culture substrate. The invention encompasses the use of any substrate which supports the growth of pluripotent cells, as well as the growth of differentiating cells, RPE progenitors, and RPE cells. Exemplary substrates include commonly-used substrates such as Matrigel, mouse embryonic fibroblast feed cell layers, human embryonic fibroblasts, human fallopian tube epithelium, or human foreskin fibroblasts feeder layers, as known in the art. Xeno-free substrates, for example, commercially available substrates such as Synthemax™ (Corning Life Sciences), CELLstart™ (Invitrogen), GELstart™ (Invitrogen), and StemAdhere™ (Primorigen) may be used. Additionally, human vitronectin, purified from human plasma or produced by recombinant expression, may serve as a xeno-free substrate for pluripotent cell growth, for example as described in Braam et al., Recombinant Vitronectin Is a Functionally Defined Substrate That Supports Human Embryonic Stem Cell Self-Renewal via αVβ35 Integrin, Stem Cells 26:2257-2265 (2008). Human-derived recombinant Laminin, for example Laminin 511 (BD) or Laminin 521 (Biolamina) may be utilized. Additionally, poly-D-lysine may act as a substrate, for example as described in Harb et al., The Rho-Rock-Myosin Signaling Axis Determines Cell-Cell Integrity of Self-Renewing Pluripotent Stem Cells. PLoS ONE 3(8): e3001 (2008).

Molecular characterization. For monitoring the stage of RPE differentiation, and for subsequent validation of RPE phenotype, the expression of various molecular markers t may be assessed. Genetic markers can be confirmed by various methods known in the art. For example, expression of molecular markers may be quantified by quantifying marker gene mRNA, for example, by the use of qPCR methods as known in the art. Alternatively, expression of molecular markers may be assessed by quantification of marker gene translation products, for example by immunoassay, for example, immunocytochemistry and immunoblot assays.

Media of the Invention

Basal Media. Culturing, including maintenance of pluripotent cells, differentiation of pluripotent cells into RPE, and expansion and maintenance of RPE cultures, is carried out in various media, as described herein. The growth media of the invention are made by adding novel combinations of additives to a basal medium. As used herein, the term "basal medium" refers to a cell growth or cell culture medium in which pluripotent cells and their differentiating/differentiated derivatives are cultured. Basal medium, as used herein, refers to any solution of salts, sugars, amino acids and growth factors which supports the growth and maintenance of pluripotent cells and their differentiated derivatives, including pluripotent cell-derived RPE cells and their progenitors.

Exemplary basal media include those known in the art, for example Dulbecco's Modified Eagle Medium mammalian cell culture medium (DMEM) (Life Technologies). Another exemplary medium is Ham's F12 medium. Another exemplary medium is a 1:1 mixture of DMEM and F12. Another exemplary basal medium is Iscove's Modified Dulbecco's Medium (IMDM, from Life Technologies). Iscove's Modified Dulbecco's Medium (IMDM) (as described in Iscove, N. N., Guilbert, L. J. and Weyman, C. (1980). Complete Replacement of Serum in Primary Cultures of Erythropoietin Dependent Red Cell Precursors [CFU-E] by Albumin, Transferrin, Iron, Unsaturated Fatty Acid, Lecithin and Cholesterol. Exp. Cell Research. 126, 121-126.

Exemplary commercially available xeno-free media include X-Vivo 10™ (Lonza Biosciences), X-Vivo 15™ (Lonza Biosciences), mTeSR2™ (Stem Cell Technologies), NutriStem™ (StemGent) and HEScGRO™ (Millipore). Lonza X-Vivo 10 supplemented with 5-40% Xeno-Free Knockout Serum Replacement (XF-KOSR™, Invitrogen) or a similar xeno-free serum replacement may also be used. Additional examples of xeno-free culture media include that described in Rajala et al., A Defined and Xeno-Free Culture Method Enabling the Establishment of Clinical-Grade Human Embryonic, Induced Pluripotent and Adipose Stem Cells, PloS ONE 5:e10246 (2010), the medium described in Swistowski et al., Xeno-Free Defined Conditions for Culture of Human Embryonic Stem Cells, Neural Stem Cells and Dopaminergic Neurons Derived from Them, PLoS ONE 4: e6233 (2009), and the medium described in Amit et al., Feeder layer- and serum-free culture of human embryonic stem cells, Biology of Reproduction 70:837 (2004). Additionally, the media described in Thompson et al., Embryonic Stem Cell Lines Derived from Human Blastocysts, Science 282:1145 (1998) or described at http://www.wicell.org/index.php?option=com_content&task=section&id=23&Itemid=273 may be modified by the replacement of fetal bovine serum or standard KOSR (knockout serum replacement) with Xeno-Free Knockout Serum Replacement (XF-KOSR™ Invitrogen) or a like xeno-free KOSR substitute. The growth medium described in U.S. Pat. No. 5,945,337, Method for Culturing CD34 Cells in a Serum-Free Medium, by Brown et al. may also be utilized.

Another exemplary basal medium is Neurobasal™ medium from Life Technologies. Other exemplary basal media include Minimum Essential Medium Eagle (MEM), Roswell Park Memorial Institute Medium 1640 (RPMI-1640, and MCDB medium.

Basal media may be supplemented with serum, for example fetal bovine serum. Alternatively, defined serum replacements may be used, for example, Knockout Serum Replacement (Life Technologies). Another exemplary serum substitute is B27 (Life Technologies). Another exemplary serum replacement is N2 supplement, which may be used at about 1% volume. Serum and serum replacements in general may be used at 1-20%, by volume.

Basal media may also include additional supplements known in the art to improve the viability of cells and the efficiency of cell cultures. L-glutamine or substitutes thereof, for example GLUTAMAX-1™ Supplement (Life Technologies) may be used to prevent ammonia buildup in cultures, for example at about 1-5 mM. Additionally, Minimum Essential Medium Eagle with non-essential amino acids (MEM-E NEAA, from Biological Industries) may be used, in concentrations of about 0.05-0.5 mM. Additionally, B-mercaptoethanol may be used to preserve proteins in the medium, for example in concentrations of about 0.05-0.5 mM.

In a preferred embodiment, a 1:1 mixture of DMEM and F12 supplemented with 1% N2 supplement, 2% B27, 2 mM GlutaMAX-I, 0.1 mM MEM NEAA is used as a basal medium.

Media Additives

The methods of the invention encompass the use of various novel media compositions. These novel media are formulated by the addition of certain additives to the basal medium. The various additives are set forth and described below.

One additive used to formulate the novel media of the invention is noggin, a protein inhibitor of bone morphogenetic protein (BMP) and TGF-Beta signaling. Recombinant noggin may be acquired from numerous commercial suppliers. Human derived recombinant noggin is preferred for the culture and differentiation of human pluripotent cells, although noggin derived from other mammalian species may be used as well. Noggin mimics may be substituted for noggin in the media. Noggin mimics encompass any compound which recapitulates the effects of noggin in the differentiation and maturation of RPE cells from pluripotent cells. Noggin mimics include modified forms of noggin, peptides encompassing the noggin binding domains, and noggin analogs comprising substituted amino acids. Exemplary noggin mimics include BMP inhibitors, i.e. any small molecule, peptide, or protein capable of inhibiting BMP pathway signaling. Exemplary BMP inhibitors include the small molecules LDN-193189 (Stemgent) and Dorsomorphin (StemRD). Proteins that inhibit BMP signaling include chordin and cerberus (R&D Systems).

Another additive used to formulate the novel media of the invention is insulin-like growth factor (IGF1). IGF1, also called Somatomedin C, is a protein similar to insulin in its molecular structure. Recombinant IGF1 may be acquired from numerous commercial suppliers. Human derived recombinant IGF1 is preferred for the culture and differentiation of human pluripotent cells, although IGF1 derived from other mammalian species may be used as well. IGF1 mimics may be substituted for IGF1 in the media. IGF1 mimics encompass any compound which recapitulates the effects of IGF1 in the differentiation and maturation of RPE cells from pluripotent cells. IGF1 mimics include modified forms of IGF1, peptides encompassing the IGF1 binding domains, and IGF1 analogs comprising substituted amino acids. Exemplary IGF1 mimics include peptide IGF-1 mimics as described in Harb et al., The Rho-Rock-Myosin Signaling Axis Determines Cell-Cell Integrity of Self-Renewing Pluripotent Stem Cells. PLoS ONE 3(8): e3001 (2008), or in U.S. patent application Ser. No. 12/659,546, by Chung et al., "Peptides having activities of insulin like growth factor-1 and their uses."

Another additive used to formulate the novel media of the invention is Dickkopf-related protein (DKK1), a secreted protein inhibitor of the WNT signaling pathway. Recombinant DKK1 may be acquired from numerous commercial suppliers. Human derived recombinant DKK1 is preferred for the culture and differentiation of human pluripotent cells, although DKK1 derived from other mammalian species may be used as well. DKK1 mimics may be substituted for DKK1 in the media. DKK1 mimics encompass any compound which recapitulates the effects of DKK1 in the differentiation and maturation of RPE cells from pluripotent cells. DKK1 mimics include modified forms of DKK1, peptides encompassing the DKK1 binding domains, and DKK1 analogs comprising substituted amino acids. Exemplary DKK1 mimics include any Wnt signaling pathway inhibitor. Wnt inhibitors may comprise small molecules, for example IWP-2, IWP-3, IWP-4, and XAV939 (all available from Stemgent). Wnt inhibitors also include peptide inhibitors of Wnt signaling, for example as described in Gregory et al., Dkk-1-derived Synthetic Peptides and Lithium Chloride for the Control and Recovery of Adult Stem Cells from Bone Marrow. Journal of Biological Chemistry, 2005, Vol. 280, No. 3, pp. 2309-2323. Secreted frizzled related proteins that act as inhibitors of Wnt signaling may also be used as DKK1 mimics, for example SFRP1, SFRP2, and others (available from R&D Systems). Wnt Inhibitory Factor 1 (WIF-1) is another protein Wnt inhibitor.

Another type of additive used to formulate the novel media of the invention is nicotinamide, a B Vitamin. Nicotinamide mimics may be substituted for nicotinamide in the media. Nicotinamide mimics encompass any compound which recapitulates the effects of nicotinamide in the differentiation and maturation of RPE cells from pluripotent cells. Nicotinamide mimics include modified forms of nicotinamide, and chemical analogs of nicotinamide. Exemplary nicotinamide mimics include benzoic acid, 3-aminobenzoic acid, and 6-aminonicotinamide. Another class of compounds that may act as nicotinamide mimics are inhibitors of poly(ADP-ribose) polymerase (PARP). Exemplary PARP inhibitors include 3-aminobenzamide, Iniparib (BSI 201), Olaparib (AZD-2281), Rucaparib (AG014699, PF-01367338), Veliparib (ABT-888), CEP 9722, MK 4827, and BMN-673.

Another additive used to formulate the novel media of the invention is basic fibroblast growth factor 1 (BFGF1). Recombinant BFGF1 may be acquired from numerous commercial suppliers. Human derived recombinant BFGF1 is preferred for the culture and differentiation of human pluripotent cells, although BFGF1 derived from other mammalian species may be used as well. BFGF1 mimics may be substituted for BFGF1 in the media. BFGF1 mimics encompass any compound which recapitulates the effects of BFGF1 in the differentiation and maturation of RPE cells from pluripotent cells. BFGF1 mimics include modified forms of BFGF1, peptides encompassing the BFGF1 binding domains, and BFGF1 analogs comprising substituted amino acids. Exemplary BFGF1 mimics include other members of the fibroblast growth factor family, for example FGF1, FGF2, FGF3, FGF4, FGF5, FGF6, FGF7, FGF8, FGF9, and FGF10. The small molecule SUN13837 may also serve as a BFGF1 substitute. Other exemplary mimics include the synthetic peptide F2A4-K-NS (as described in Lin et al., Synthetic peptide F2A4-K-NS mimics fibroblast growth factor-2 in vitro and is angiogenic in vivo, International Journal of Molecular Medicine 17:833-839 (2006)), and trichostatin A (as described in Durcova-Hills et al., Reprogramming Primordial Germ Cells into Pluripotent Stem Cells. PLoS ONE 3(10) (2008)).

Another additive used to formulate the novel media of the invention is Activin A. Recombinant Activin A may be acquired from numerous commercial suppliers. Human derived recombinant Activin A is preferred for the culture and differentiation of human pluripotent cells, although Activin A derived from other mammalian species may be used as well. Activin A mimics may be substituted for Activin A in the media. Activin A mimics encompass any compound which recapitulates the effects of Activin A in the differentiation and maturation of RPE cells from pluripotent cells. Activin A mimics include modified forms of Activin A, peptides encompassing the Activin A binding domains, and Activin A analogs comprising substituted amino acids. Exemplary Activin A mimics include Activin AB, and Activin B and members of the transforming growth factor beta (TGFB) family, for example, BMP-4, BMP-7 and TGF-beta1.

Another additive used to formulate the novel media of the invention is SU5402, an FGF signaling inhibitor. SU5402 mimics may be substituted for SU5402 in the media. SU5402 mimics encompass any compound which recapitulates the effects of SU5402 in the differentiation and maturation of RPE cells from pluripotent cells. SU5402 mimics include modified forms of SU5402, and chemical analogs of SU5402. Exemplary SU5402 mimics include any FGF signaling inhibitor. For example, the protein sprouty 2 may serve as an SU5402 mimic Other SU5402 mimics include small molecule inhibitors of FGF signaling such as AZD4547 and PD173074 (Stemgent).

Another additive used to formulate the novel media of the invention is vasoactive intestinal peptide (VIP), a cyclic AMP upregulator. Recombinant VIP may be acquired from numerous commercial suppliers. Human derived recombinant VIP is preferred for the culture and differentiation of human pluripotent cells, although VIP derived from other mammalian species may be used as well. VIP mimics may be substituted for VIP in the media. VIP mimics encompass any compound which recapitulates the effects of VIP in the differentiation and maturation of RPE cells from pluripotent cells. VIP mimics include modified forms of VIP, peptides encompassing the VIP binding domains, and VIP analogs comprising substituted amino acids. Exemplary VIP mimics include any cyclic AMP upregulator. VIP mimics include, for example, small molecules such as forskolin and rolipram.

Specific Media Compositions

In some embodiments, the invention comprises six novel media, used in various stages of RPE differentiation and propagation, as described below.

MEDIUM 1. Medium 1 comprises basal medium supplemented with biologically active concentrations of the following additives: Noggin, for example, at 1 to 100 ng/ml; IGF1, for example, at 1 to 100 ng/ml; DKK1, for example, at 1 to 50 ng/ml; and Nicotinamide, for example, at 1 to 100 mM. In Medium 1, noggin or DKK1 may be used in excess and there is no actual upper limit to the amount of that may be used. Nicotinamide is not necessary for RPE differentiation, and may be omitted, but it is included to speed up the RPE differentiation process.

In a preferred version of Medium 1, the additives are included at the following concentrations: Noggin, at 50 ng/ml; IGF1, at 10 ng/ml; DKK1, at 10 ng/ml; and Nicotinamide, at 10 mM.

Medium 2

Medium 2 comprises basal medium supplemented with biologically active concentrations of the following additives: Noggin, for example, at 1 to 100 ng/ml; IGF1, for example, at 1 to 100 ng/ml; DKK1, for example, at 1 to 50 ng/ml; and Nicotinamide, for example, at 1 to 100 mM, and BFGF, for example at, at 1 to 20 ng/ml.

As in Medium 1, In Medium 2 noggin or DKK1 may be used in excess and there is no actual upper limit to the amount of that may be used. Nicotinamide is again not necessary and may be omitted, but it is included to speed up the RPE differentiation process. Likewise, BFGF may also be omitted, however its inclusion in the medium improves the yield and efficiency of the process.

In a preferred version of Medium 2, the additives are included at the following concentrations: Noggin, at 10 ng/ml; IGF1, at 10 ng/ml; DKK1, at 10 ng/ml; Nicotinamide, at 10 mM; and bFGF, 5 ng/ml.

Medium 3

Medium 3 comprises basal medium supplemented with biologically active concentrations of the following additives: IGF1, for example, at 1 to 100 ng/ml; DKK1, for example, at 1 to 50 ng/ml; and Activin A, for example, at 10 to 200 ng/ml. In Medium 3, DKK1 may be used in excess and there is no actual upper limit to the amount of that may be used.

In a preferred version of Medium 3, the additives are included at the following concentrations: IGF1, at 10 ng/ml; DKK1, at 10 ng/ml; and Activin A, at 100 ng/ml.

Medium 4

Medium 4 comprises basal medium supplemented with biologically active concentrations of the following additives: Activin A, for example, at 10 to 200 ng/ml; SU5402, for example at 1 to 100 µM; and VIP, for example at 0.1 to 100 µM. In Medium 4, SU5402 may be used in excess and there is no actual upper limit to the amount of that may be used. VIP is not necessary and may be omitted, but its inclusion will help to speed up the RPE differentiation process.

In a preferred version of Medium 4, the additives are included at the following concentrations: Activin A, at 100 ng/ml; SU5402, at 10 µM; and VIP, at 1 µM.

It will be understood by one of skill in the art that mimics of any specific additive used in the above media formulations may be substituted for the original additive in a biologically equivalent amount. For purposes of this disclosure, a "biologically equivalent amount" means a quantity of such mimic that has the same biological effect on pluripotent cells differentiating into RPE cells as the enumerated quantity of the named additive. For example, if a medium is described as containing 10 ng/ml of additive X, it will be understood by one of skill in the art that an additive X mimic may be utilized instead, the additive X mimic being used in an amount sufficient to replicate the biological effect using 10 ng of additive X. Such biologically equivalent amount may be readily determined by one of skill in the art by various methods. If the mimic has a protein or chemical structure that is very similar to that of the original additive, the mimic may be used in the same or nearly the same amount as the additive. Alternatively, the mimic may be used at the concentration at which it is known to have a biological effect, as known in the art. Alternatively, the mimic may be tested in an RPE differentiation protocol at various concentrations, and the concentration range at which the effects of the original additive are recapitulated will be the proper range for use of the mimic.

Additionally, it will be understood by one of skill in the art that the invention comprises the use of subsets of the media additives described for each media composition. For example, a medium omitting one or more of the constituents of Media 1, Media 2, Media 3, Media 4, the RPE Maturation Media, or the RPE Proliferation Medium will still fall within the scope of the invention.

Protocol for RPE Production

In certain embodiments, the timing of inclusion or exclusion of various media formulations or media additives in the culture media is based on the expression of molecular markers. Molecular marker expression may be assayed by various standard tools known in the art, for example by quantification of messenger RNA, by quantification of gene product proteins, or functional assays (e.g. enzymatic activity of expressed proteins. Molecular markers include Paired box protein (Pax6) (also known as aniridia type II protein (AN2) or oculorhombin is a that in humans is encoded by the PAX6 gene; the Rax homeobox gene (also known as Rx) encoded by the RAX gene; LIM/homeobox protein (Lhx2), a protein that in humans is encoded by the LHX2 gene; Homeobox protein SIX3, a protein that in humans is encoded by the SIX3 gene; tyrosinase enzyme is encoded by the TYR gene; Microphthalmia-associated transcription factor (MITF); Human cationic trypsinogen, encoded by the TRYP1 gene; Trypsin-1, also known as cationic trypsinogen, in humans is encoded by the PRSS1 gene; trypsin-2 (anionic trypsinogen), in humans encoded by the PRSS2 gene; Melanocyte protein PMEL 17 also known as premelanosome protein (PMEL17) or silver locus protein homolog (SILV), in humans is encoded by the PMEL gene; ceh-10 homeo domain containing homolog (Chx10), also known as Ceh-10 homeodomain-containing homolog; and Bestrophin-1, that in humans is encoded by the BEST1 gene.

To initiate the RPE production protocol, pluripotent cells commence culture in Medium 1. The initiation of culture in Medium 1 starts the protocol, and the time is referred to as "Day 0." In an exemplary embodiment, the protocol is initiated by transferring clumps of pluripotent cells, maintained as known in the art, to a new culture vessel, for example, the well of a 6-well plate, such transferred cells being plated to cover 50-75% of the culture well. Thereafter, Medium 1 in an appropriate amount, for example 2 ml for the well of a standard six well plate, is added. On Day 1 (about 24 hours after initiation of the protocol), it is preferred that the medium in the culture vessel be replenished with new Medium 1. Culture in Medium 1 is theorized to commence neural induction in the pluripotent cells. Cells begin to lose pluripotent morphology (high nucleus to cytoplasm ratio) and extend processes in radial orientation.

Next, the medium in the culture vessel is switched to Medium 2. The transition to Medium 2 may take place as early as 24 hours after the commencement of culture in Medium 1 to as late as 3 days after commencement of culture in Medium 1 In a preferred embodiment, the transition to Medium 2 is made on or about Day 2 (i.e. about 48 hours after the commencement of culture in Medium 1). Alternatively, the transition to Medium 2 may be made within 0-24 hours of the first detectable expression or significant upregulation of any of the retinal progenitor markers Pax6, Rax, Lhx2, Six3, or the detection of any other molecular, physiological, or morphological markers of neural induction.

During culture in Medium 2, the cultured cells are theorized to be undergoing retinal progenitor specification or early eye field differentiation.

Next, the medium in the culture vessel is switched to Medium 3. The transition to Medium 3 may take place as early as Day 2 to as late as Day 6. In a preferred embodiment, the transition to Medium 3 is made on or about Day 4. Alternatively, the transition to Medium 3 may be made upon observing a substantial increase (e.g. 10-fold) in the expression of any of the retinal progenitor markers Pax6, Rax, Lhx2, or Six3. Alternatively, the transition to Medium 3 may be made within 0-24 hours of first observing the expression of Mitf or Chx10 expression. Alternatively, the transition to Medium 3 may be made upon observing the formation of rosette structures, for example, structures described in Panagiotakos et al., Human ES cell-derived neural rosettes reveal a functionally distinct early neural stem cell stage. Genes Dev. 2008 22(2):152-65. Alternatively, the transition to Medium 3 may be made shortly after the detection of any other molecular, physiological, or morphological markers of retinal progenitor specification or early eye field differentiation. During culture in Medium 3, it is theorized that the cultured cells are undergoing RPE specification.

Next, the medium in the culture vessel is switched to Medium 4. The transition to Medium 4 may take place as early as Day 5 to as late as Day 8. In a preferred embodiment, the transition to Medium 4 is made on or about Day 6. Alternatively, the transition to Medium 3 may be made upon observing a substantial decrease in the expression of Mitf, or upon the detection of expression of any RPE associated marker such as Tyrosinase (TYR), melanocyte protein PMEL 17 (SILV), cellular retinaldehyde-binding protein (CRALBP), Tryp1, Tryp2, or bestrophin. Alternatively, the transition to Medium 3 may be made upon observing the flattening of rosette structures into sheets of immature RPE cells.

Upon transition to Medium 4, the differentiating cells may thereafter be maintained in Medium 4, with the medium preferentially being changed every other day.

The timing of the media transitions will be delayed if nicotinamide or a nicotinamide mimic is not used in Media 1 and/or Media 2. Without nicotinamide (or a mimic), the transition from Medium 1 to Medium 2 should occur on or about Day 4; the transition to Medium 3 should take place on or about Day 8, and the transition to Medium 4 should take place on or about Day 12.

It will be understood by one of skill in the art that the invention is not limited to the specific compositions of Medium 1, Medium 2, Medium 3, or Medium 4, and that the invention encompasses the use of the various media constituents (and their mimics and/or equivalents) singly, or in combination with other media additives. For example, a medium for the differentiation of pluripotent cells may comprise one or more of noggin, DKK1, IGF1, BFGF, nicotinamide, SU5402, VIP, or Activin A.

In one embodiment, the invention comprises the use of a basal medium for the culture of pluripotent cells or cells differentiating into RPE cells, such basal medium optionally supplemented with a biologically active concentration of noggin and/or nicotinamide and such basal medium not containing a biologically active concentration of Activin A. At various time points (e.g. daily), the expression of one or more of the following molecular markers is monitored in the cultured cells: Pax6, Rax, Lhx2, Six3, Mitf, and Chx10. After observing a substantial increase (e.g. 10-fold) in the expression of any of the retinal progenitor markers Pax6, Rax, Lhx2, or Six3, or 0-24 hours after first observing the expression of Mitf or Chx10 in the cultured cells, the cultured cells are thereafter cultured in a medium that does not contain either noggin or nicotinamide, and which optionally contains a biologically effective concentration of Activin A. Alternatively, the exclusion of noggin and/or nicotinamide or the inclusion of Activin A may be made upon observing the formation of rosette structures.

In another embodiment, pluripotent cells or pluripotent cells differentiating into RPE cells are cultured in a medium which does not contain a biologically active concentration of BFGF. At various time points (e.g. daily), the expression of one or more of the following molecular markers is monitored in the cultured cells: Pax6, Rax, Lhx2, and Six3. Upon the first detectable expression of one or more of the markers Pax6, Rax, Lhx2, or Six3, the cultured cells are switched to a medium containing a biologically active concentration of BFGF.

In another embodiment, the invention comprises the use of a basal medium for the culture of pluripotent cells differentiating into RPE cells, such basal medium optionally supplemented with a biologically active concentration of DKK1 and/or IGF1 and such basal medium not containing a biologically active concentration of SU5402 or VIP. At various time points (e.g. daily), the expression of one or more of the following molecular markers is monitored in the cultured cells: Mitf, TYR, PMEL17, CRALBP, Tryp1, Tryp2, or bestrophin. After observing a substantial decrease in the expression of Mitf, or upon the detection of expression of TYR, PMEL 17, CRALBP, Tryp1, Tryp2, or bestrophin, the cultured cells are transitioned to a medium which does not contain an biologically active concentration of DKK1 or IGF1, and which optionally contains a biologically active concentration of SU5402 and/or VIP. Alternatively, the exclusion of DKK1 and/or IGF1 and/or the inclusion of SU5402 and/or VIP may be made upon observing the flattening of rosette structures into sheets of immature RPE cells.

In the preferred protocol (with nicotinamide or a mimic in both Media 1 and Media 2), by about Day 10, sheets of immature RPE cells become noticeable, comprising planar cells with "cobblestone" morphology, i.e. a single-cell layer flat sheet mosaic of polygonal and hexagonal shaped cells that is characteristic of native RPE cells. The RPE morphology becomes quite distinct by about Day 14. Visible pigmentation generally appears sometime between Day 9 and Day 16.

At any time after Day 10, X-Vivo™ 10 medium (Lonza) may be utilized. X-Vivo 10 may be utilized for the continued maturation of RPE cells, and the expansion and/or maintenance of differentiated RPE cells.

By about Day 14, the majority of cells (>75%) will typically have the distinct cobblestone morphology of RPE cells and light pigmentation will be observable in some or most of the cells. The media of the invention appears to be both directive and selective for RPE. Cells having non-RPE morphology may be visible at early in the differentiation process, but they typically die off by Day 28. The pigmentation of the maturing RPE cells will continue to increase over time, generally reaching a maximum at about Day 30 onward.

Maturation of RPE cells occurs along a continuum of increasing maturity. Lightly pigmented cells or cells with cobblestone morphology would best be described as immature RPE cells. As cells mature over time, pigmentation increases. Maturation may also be assessed by changes in gene expression over time, with the appearance of, or an increase in the expression levels of RPE markers, as known in the art, being indicative of a more mature phenotype. Maturation may also be assessed by functional assays, as known in the art. For purposes of this disclosure, maturation may be assessed by pigmentation, molecular marker expression, or functional assays.

RPE maturity may be assessed by the presence of genetic markers associated with functional RPE phenotype, such as MitF, Tyrosinase, Tyrp1, Tyrp2, Best1, CRALBP, and RPE65.

Alternatively, the maturity of RPE cells may be assessed by functional assays. For example, in normal RPE cell function, RPE cells phagocytose shed rod outer segments (ROS), preventing their accumulation. Ability to phagocytose ROS is indicative of functional RPE. Established assays to measure the ability of cultured putative RPE cells to phagocytose ROS are known in the art, for example as described in detail in Haruta et al., In Vitro and In Vivo Characterization of Pigment Epithelial Cells Differentiated from Primate Embryonic Stem Cells, IVOS 45:1020-1045 (2004) and Carr et al., Molecular characterization and functional analysis of phagocytosis by human embryonic stem cell-derived RPE cells using a novel human retinal assay, Mol Vis. 15: 283-295 (2009). Additionally, mature RPE are known to efficiently convert trans retinol to 11-cis retinol. Assays for the ability to convert trans retinol to 11-cis retinol are known in the art. Additional assays for maturity include assaying for the polarized secretion of growth factors and tight junctions creating an electrical barrier, as described in Vaajasaari et al Mol. Vis. 2011 Toward the defined and xeno-free differentiation of functional human pluripotent stem cell-derived retinal pigment epithelial cells.

Maturity and pigmentation is speeded up by the use of VIP in the maintenance culture medium (e.g. Media 4, or a maintenance medium to which the cells are transitioned after Media 4), for example at a concentration of 0.1 to 100 µM, with a preferred concentration of 1 µM. Cultures without VIP will tend to increase pigmentation and reach maturity at a lower rate.

Pigmentation may be promoted by changing the medium to X-Vivo 10 medium (Lonza Biosciences) after about Day 12. By about Day 30, dark pigmentation will be widespread in cultures switched to X-Vivo 10. However, changing to this medium may result in the proliferation of non-RPE type cells, reducing the percentage of RPE-type cells to about 50% of the culture vessel area.

Replating, Expansion, and Maturation of RPE Cells. At any time after Day 10, the RPE cells may be passaged to fresh substrate, for expansion of cultures or to enrich cultures in RPE. For example, RPE cell cultures may be enriched by mechanically removing any non-RPE cells, for example by pipette tip, followed by replating the maturing RPE cells on fresh substrate, as described below.

In one embodiment, the RPE sheets can be lightly treated with protease and broken down into small pieces. For example, proteases such as dispase or collagenase may be used. For example, dispase at a concentration of 1.5 U/mL is added to the culture vessel, for example 1 ml per well in a standard six-well plates (well diameter of 9.5 cm$^2$). RPE sheets will begin to dissociate from the substrate after about 5 minutes at 37 degrees C. These sheets of cellular monolayer may then be aspirated using a 5ml pipette and gently triturated to dissociate the cells into small sections which are then placed on fresh substrate. Replated sections of monolayer may be plated at any density, for example at 5%, 10%, 25%, 50%, 75% or greater coverage of the new substrate. A preferred density is in the range of 50% coverage of the new substrate. Replated sections of RPE monolayers will typically maintain their differentiated state in the middle, grow to confluence from the edges, and continue maturation towards higher levels of pigmentation.

Alternatively, maturing RPE cell monolayers may be dissociated to single cells by treatment with a protease or other dissociation agent. In an exemplary embodiment, protease TrypLE is used, at the concentration supplied by Life Technologies, for example with 1 ml of the protease solution being added per well in a standard six-well plate (well diameter of 9.5 cm$^2$). Cells are exposed to the protease for 5 minutes at 37 degrees C., triturated into single cells using a P1000 pipetman, aspirated from the culture vessel, washed in PBS buffer, centrifuged, and resuspended in medium.

The concentration of dissociated single RPE cells in suspensions may be quantified by any means, including the use of cell counters, hemacytometers, and other cell quantification methods known in the art. For example, a cell counter with gating diameter set between 6 and 20 µm may be used. The single cells may be then be replated at any desired density. For example, for expansion of the cells, they may be replated at a density of about $2.5 \times 10^4$ cells/cm$^2$ and passaged when 90% confluence is reached. For maturation, cells may be seeded at a density of about $1 \times 10^5$ cells/cm$^2$.

Replated cells may be grown on any suitable combination of substrate and medium that is known for the maintenance of RPE cultures. For example, the cells may basal medium supplemented with FBS or B27, X-Vivo 10, or any other compatible media known in the art. Other exemplary media for the growth and culture of RPE cells are described in Maminishkis et al. Confluent monolayers of cultured human fetal retinal pigment epithelium exhibit morphology and physiology of native tissue. Invest Ophthalmol Vis Sci. (2006); Gamm et al. A novel serum-free method for culturing human prenatal retinal pigment epithelial cells. Invest Ophthalmol Vis Sci. 2008; Ahmado et al. Induction of differentiation by pyruvate and DMEM in the human retinal pigment epithelium cell line ARPE-19. Invest Ophthalmol Vis Sci. 2011; Hu and Bok. A cell culture medium that supports the differentiation of human retinal pigment epithelium into functionally polarized monolayers. Mol Vis. 2001.

Alternatively, the replated cells may be expanded and maintained on a novel proliferation medium developed by the inventors of the present disclosure ("RPE Proliferation Medium." The RPE Proliferation Medium may be used for the proliferation, maintenance, or expansion of RPE cells derived from any source, for example, RPE cells derived from the protocols disclosed herein, RPE cells derived from other RPE production protocols known in the art, or native RPE cells isolated from retinas, e.g. fetal or adult eye tissues. During proliferation, RPE cells that are cultured in medium containing fetal bovine serum tend to undergo an epithelial to mesenchymal-like transition and after several passages are unable to regain RPE morphology. It has been advantageously discovered that the use of a serum-free medium for RPE proliferation does not cause this undesired transition. The novel RPE Proliferation Medium is composed of a basal medium, for example, Iscove's Modified Dulbecco's Medium (as known in the art), supplemented with one or more of the following: Insulin, for example at about 1-100 µg/ml; Holo-transferrin, for example at about 1-10 µg/ml; Selenium, for example at about 0.001-0.3 µg/ml; Albumin, for example at about 4 µg/ml to 10 µg/ml; and Chemically Defined Lipid Concentrate (Life Technologies), for example present at a dilution of about 1:100 to 1:2000.

Selenium may be omitted. If selenium is already present in the basal medium, it should be accounted for when determining the amount of selenium to add to the medium. For example, selenium is already present in IMDM medium at about 0.17 µg/ml, and supplemental amounts of 0.001 to 0.1 may be added in addition to the selenium already present in this medium. Linoleic acid and cholesterol, for example at about 10 µg/ml and 4-500 µg/ml, respectively, may be used in place of Life Technologies Chemically Defined Lipid Concentrate. It will be understood by one of skill in the art that other biologically equivalent basal medium and/or supplements may be substituted for the medium and supplements listed above.

RPE grown in the RPE Proliferation Medium described above tend to grow in clonal clusters and maintain a more RPE-like morphology during proliferation whereas RPE cells grown in medium containing serum take on a fibroblastic, elongated morphology and do not grow in contact with one another.

In a preferred version of the RPE Proliferation Medium, a basal medium (e.g. IMDM) is supplemented with the following: Insulin, at about 10 µg/ml; Holo-transferrin, at about 5.5 µg/ml; Selenium, at about 0.18 µg/ml (0.0067 µg/ml if added to IMDM); Albumin, at about 4 µg/ml; and Chemically Defined Lipid Concentrate (Life Technologies), present at a dilution of about 1:1000.

Maturation of Cultured RPE Cells

For efficient and optimal maturation, a novel RPE maturation medium has been developed by the inventors of the present disclosure ("RPE Maturation Medium"). The RPE Maturation Medium is composed of a basal medium (e.g. Iscove's Modified Dulbecco's Medium), supplemented with B27 (for example, as described in Brewer et al., Optimized survival of hippocampal neurons in B27-supplemented Neurobasal™, a new serum-free medium combination, Neurosci. Res. 35: 567-576 (1993)), or for example Life Technologies 50×B27 supplement at a dilution of 1:50, and also optionally supplemented with taurine, for example at a concentration of 1-500 µg/ml, with a preferred concentration of 250 µg/ml. A combination of progesterone (for example at 2 uM), Vitamin A (for example at 0.5 uM) and triiodothyronine (for example at 10 nM) may be used in place of B27.

The novel RPE Maturation Medium is used as follows. RPE cells growing on the RPE Proliferation Medium are maintained on the same substrate until one week after confluence has been reached, at which time the RPE Maturation Medium is substituted for the RPE Proliferation Medium. Within 2-3 weeks after the medium change, the RPE cells become mature at high frequency, with maturity described and assayed as set forth above. Both the rate of maturation, and the percentage of cells becoming mature is significantly increased by the use of this medium relative to RPE cells that continue culture in the RPE Proliferation Medium.

Rock Inhibitors

It has been advantageously discovered by the inventors of the present disclosure that the culture of proliferating RPE cells may optionally employ media supplemented with a rho-kinase (ROCK) inhibitor. The use of ROCK inhibitors may advantageously be employed in the maintenance, expansion, and maturation of RPE cells derived from any source, for example, from pluripotent cells or native RPE cells isolated from retinas, e.g. from the eyes of patients, donors, or other sources, e.g. fetal or adult eye tissues.

Exemplary ROCK inhibitors include Y-27632, thiazovivin, GSK429286A, and Fasudil. Y-27632 may be used at a concentration ranging from 500 nM to 50 uM. Y-27632 is a selective inhibitor of the Rho associated kinase, p160ROCK and ROCK-II with a Ki value of 140 nm Y-27632 additionally inhibits PKC, cAMP-dependent protein kinase and myosin light-chain kinase but with greatly diminished Ki values, 26, 25 and >250 µM, respectively.

ROCK inhibitors may be used in the maturation, maintenance, expansion, or proliferation of RPE cells by including a physiologically effective amount of ROCK inhibitor as a supplement in any media known for the maintenance, proliferation, and maturation of RPE cells. For example Y27632 may be used at a concentration ranging from about 500 nM to 50 uM. The use of ROCK inhibitors allows replated RPE cells to retain their RPE phenotype during more passages and expansions than replated cells in media lacking ROCK inhibitors. For example, in the protocol described herein, the use of the ROCK inhibitor-supplemented media for cells replated between Day 10 and about Day 20 substantially increases the survival and viability of the cells. When RPE cells are dissociated into single cells, they often lose many of their RPE characteristics when subsequently seeded and proliferated on new substrates. Culturing re-seeded single cells in medium supplemented with ROCK inhibitor improves both survival and expansion. Inclusion of ROCK inhibitor during serial passaging of RPE allows far greater expansion of cells than serial passaging without ROCK inhibitor. For example, cells cultured in XVIVOT™10, plated at a density of $2.5 \times 10^4$ cells/cm$^2$ and passaged when cells reach approximately 90% confluence can be passaged greater than 14 times when ROCK inhibitor is included. If ROCK inhibitor is not included, cultures stop dividing at passage 4-7. When re-differentiation is desired, the ROCK inhibitor may be removed from the medium, for example when confluence is reached. Thereafter, the cells will typically re-differentiate to mature RPE cells within two to four weeks. ROCK inhibitors have previously been used for survival and expansion of hESC, corneal endothelial cells, keratinocytes and other epithelial cells, for example as described in Watanabe et al., A ROCK inhibitor permits survival of dissociated human embryonic stem cells. Nat. Biotechnol. 25: 681-686 (2007); and Okumura et al., The new therapeutic concept of using a Rho kinase inhibitor for the treatment of corneal endothelial dysfunction. Cornea 30(Suppl 1):S54-S59 (2011), but have not been previously used in the manner disclosed herein.

Alternatively, inhibitors of the ROCK-Myosin II pathway may be used in place of ROCK inhibitors. For example, Blebbistatin, an inhibitor of myosin light chain II may be used at a concentration between 1 uM and 100 uM. In a preferred embodiment, Blebbistatin is used at 10 uM.

Mature RPE produced by the methods of the invention in general may be passaged and expanded for as many as 14 passages with the inclusion of ROCK inhibitor. Thereafter, the cells may be used for research purposes, for therapeutic uses, or may be cryopreserved for later use.

In some embodiments, the invention comprises a method of using Media 1, Media 2, Media 3, and Media 4 in sequence to promote fast differentiation of RPE from pluripotent cells. In another embodiment, the invention comprises a specific media composition, for example Media 1, Media 2, Media 3, Media 4, the RPE Maturation Media, or the RPE Proliferation Medium. In other embodiments, the invention comprises kits which are combinations of the above-listed media. For example, in one embodiment, the invention comprises a kit made up of Media 1, Media 2, Media 3, and Media 4. In other embodiments, the invention comprises media supplement kits made up of the media additives for a specific media, for example, the additives which are combined with a basal media to form Media 1, Media 2, Media 3, Media 4, the RPE Maturation Media, or the RPE Proliferation Medium. For example, the media supplement kit for Media 1 would comprise DKK1, noggin, IGF1, and optionally, nicotinamide. Media supplement kits could take the form of a single solution containing all the additives of a given medium, or could take the form of multiple vessels containing different additives. In such media supplement kits, the additives are present in such amounts that when a specified amount of the media additive kit contents is added to a specified volume of basal medium, an effective media composition is formed (e.g. Media 1, Media 2, etc.).

EXAMPLE 1

In this Example, the media and methods of the invention are demonstrated to rapidly produce RPE cells. Further details on the experiments described in this Example 1 are described in Buchholz et al., Rapid and Efficient Directed Differentiation of Human Pluripotent Stem Cells Into Retinal Pigmented Epithelium, Stem Cells Trans Med 2(5): 384-393 (2013).

Pluripotent Stem Cell Culture

The human embryonic stem cell line H9 (WiCell Research Institute, Madison, Wis., http://www.wicell.org) was maintained in Dulbecco's Modified Eagle's Medium: Nutrient Mixture F-12 (DMEM/F12) containing 2 mM GlutaMAX-I, 20% knockout serum replacement, 0.1 mM Modified Eagle's Medium Non-Essential Amino Acids (MEM NEAA), 0.1 mM Beta-mercaptoethanol (Invitro-gen, Carlsbad, Calif., http://www.invitrogen.com) and 4 ng/ml bFGF (Peprotech, Rocky Hill, N.J., http://www.peprotech-.com) on a mitomycin C (Sigma-Aldrich, St. Louis, Mo., http://www.sig-maaldrich.com)-treated mouse embryonic fibroblast feeder layer. H9s for flow cytometry were grown on growth factor-reduced Matrigel (BD Biosciences, San Diego, Calif., http://www.bdbiosciences.com) in mTESR1 (StemCell Technologies, Vancouver, BC, Canada, http://www.stemcell.com) medium. The human embryonic stem cell line UCSF4 (NIH registry no. 0044, University of California, San Francisco) was maintained on growth factor-reduced Matrigel (BD Biosciences) in mTESR1 medium (StemCell Technologies). The induced pluripotent stem cell line iPS(IMR90)-4 (IMR904) was maintained in DMEM/F12 containing 2 mM GlutaMAX-I, 20% knock-out serum replacement, 0.1 mM MEM NEAA, 0.1 mM Beta-mercaptoethanol (Invitrogen) and 100 ng/ml recombinant zebrafish bFGF on a mitomycin C (Sigma-Aldrich)-treated mouse embryonic fibroblast feeder layer.

Differentiation Into Retinal Pigmented Epithelium

Pluripotent stem cells were passaged directly onto Matrigel (BD Biosciences) in DMEM/F12 with 1×B27, 1×N2, and 1×NEAA (Invitrogen). From days 0 to 2, 50 ng/ml Noggin, 10 ng/ml Dkk1, and 10 ng/ml IGF1 (R&D Systems Inc., Minneapolis, Minn., http://www.rndsystems.com) and in some experiments 10 mM nicotinamide or 5 mM 3-aminobenzamide (Sigma-Aldrich) were added to the base medium. From days 2 to 4, 10 ng/ml Noggin, 10 ng/ml Dkk1, 10 ng/ml IGF1, and 5 ng/ml bFGF and in some experiments 10 mM nicotinamide or 5 mM 3-aminobenzamide were added to the base medium. From days 4 to 6, 10 ng/ml Dkk1 and 10 ng/ml IGF1 and in some experiments 100 ng/ml Activin A (R&D Systems) were added to the base medium. From days 6 to 14, 100 ng/ml Activin A, 10 μM SU5402 (EMD Millipore, Darmstadt, Germany, http://www.emdmillipore.com), and 1 mM VIP (Sigma-Aldrich) were added to the base medium. Control experiments were also performed in base media alone (DMEM/F12, B27, N2, and NEAA).

The cells were mechanically enriched by scraping away cells with non-RPE morphology. Subsequently, the remaining RPE were digested using TrypLE Express (Invitrogen) for ~5 minutes at 37° C. The cells were passed through a 30-μm single-cell strainer and seeded onto Matrigel-coated tissue culture plastic, Transwell membranes (Corning Enterprises, Corning, N.Y., http://www.corning.com), or CC2-treated chambered slides. Enriched cells were cultured in DMEM-high glucose with 1% fetal bovine serum (FBS), GlutaMAX, and sodium pyruvate (Invitrogen) for 30 days, as described in Ahmado A, Carr A J, Vugler A A et al. Induction of differentiation by pyruvate and DMEM in the human retinal pigment epithelium cell line ARPE-19. Invest Ophthalmol Vis Sci 2011; 52:7148-7159.

Hs27 and cultured fetal human RPE were cultured on Matrigel-coated Transwell membranes in DMEM-high glucose with 1% FBS, GlutaMAX, and sodium pyruvate (Invitrogen). MeWo cells were cultured in DMEM/F12 GlutaMAX1 (Invitrogen) with 10% fetal bovine serum (HyClone, Logan, Utah, http://www.hyclone.com).

Quantitative Real-Time Polymerase Chain Reaction Total RNA of RPE marker genes was isolated using primers based upon the mRNA sequences of such genes. QPCR methods were carried out with the RNeasy Plus Mini Kit (Qiagen, Hilden, Germany, http://www.qiagen.com). cDNA was synthesized from 1 μg of RNA using the iScript cDNA Synthesis Kit (Bio-Rad, Hercules, Calif., http://www.bio-rad.com). Primer pairs were designed to create a 75-200-base pair product (Beacon Design 4.0; Premier Biosoft International, Palo Alto, Calif., http://www.premierbiosoft.com). Quantitative real-time polymerase chain reaction (PCR) was carried out on a Bio-Rad MyIQ Single Color Real-Time PCR Detection System using the SYBR Green method, as described in Woo T H, Patel B K, Cinco M et al. Identification of *Leptospira biflexa* by real-time homogeneous detection of rapid cycle PCR product. J Microbiol Methods 1999; 35:23-30. Triplicate 20-μl reactions were run in a 96-well plate with half of the cDNA synthesis reaction used per plate. Primer specificity was confirmed by melting temperature analysis, gel electrophoresis, and direct sequencing (Iowa State DNA Facility, Ames, Iowa). The data were normalized to the geometric mean of the "housekeeping" genes: glyceraldehyde phosphate dehydrogenase (GAPDH), hydroxymethylbilane synthase (HMBS), and glucose phosphate isomerase (GPI), as described in Radeke M J, Peterson K E, Johnson L V et al. Disease susceptibility of the human macula: Differential gene transcription in the retinal pigmented epithelium/choroid. Exp Eye Res 2007; 85:366-380.

Immunocytochemistry

The cells were grown on Matrigel-coated 12-well tissue culture plates (days 0-14) or enriched onto Matrigel-coated chambered slides and cultured for 1 month. For fixation, the plates and slides were washed with phosphate-buffered saline (PBS), fixed with 4% paraformaldehyde in 0.1 M sodium cacodylate buffer, pH 7.4, for 15 minutes at 4° C., and stored in PBS at 4° C. until labeling. The slides were washed with PBS, blocked with PBS containing 5% BSA and 0.1% NP40 in PBS for 1 hour at 4° C., treated with ice-cold 90% methanol for 5 minutes, and incubated with primary antibodies overnight at 4° C. The slides were incubated with an appropriate Alexa Fluor (Invitrogen)-conjugated secondary antibody (1:300) for 30 minutes at 4° C., stained with Hoechst (2 μg/ml) (Invitrogen) for 5 minutes at room temperature, washed with PBS, and then imaged at room temperature using an Olympus IX71 fluorescence microscope or an Olympus Fluoview FV10i confocal microscope (Olympus, Center Valley, Pa., http://www.olympusamerica.com).

Flow Cytometry

The samples were fixed in 4% paraformaldehyde in PBS (Electron Microscopy Sciences, Hatfield, Pa., http://www.emsdiasum.com/microscopy) and permeabilized with 0.2% Triton X-100 (Roche, Indianapolis, Ind., http://www.roche.com). The samples were labeled with primary or isotype control antibodies for 30 minutes at 4° C. Primary and isotype control antibodies that were not conjugated to fluorophores were labeled with fluorophore-conjugated secondary antibodies for 30 minutes at 4° C. The labeled samples were run on an Accuri C6 flow cytometer with CFlow collection software (BD Biosciences). Data analysis was performed on FCS Express 4 Flow Research Edition (De Novo Software, Thornhill, ON, Canada, http://www.denovosoftware.com). The positive percentage was based on a background level set at 1% positive expression in samples labeled with isotype control antibodies.

Rod Outer Segment Phagocytosis

Rod outer segment (ROS) phagocytosis assays were performed as previously described in Lin H, Clegg D O. Integrin alphavbeta5 participates in the binding of photoreceptor rod outer segments during phagocytosis by cultured human retinal pigment epithelium. Invest Ophthalmol Vis Sci 1998; 39:1703-1712. Bovine eyes were obtained fresh from Sierra Medical Inc. (Whittier, C A, http://www.sierramedical.com); ROSs were purified from retinal extracts and fluorescently labeled using the FluoReporter FITC Protein Labeling Kit (Invitrogen). The cells were seeded in quadruplicate on gelatin-coated wells in a 96-well plate at a concentration of 25,000-50,000 cells per well and allowed to grow to confluence for 4 weeks. The cells were then challenged with $1\times10^6$ fluorescein isothiocyanate-labeled ROSs per well with or without 50 μg/ml anti-αvβ5 (ab24694; Abcam, Cambridge, U.K., http://www.abcam.com) or 50 μg/ml IgG1 control (ab9404; Abcam) for 5 hours at 37° C. in 5% CO2. The wells were then vigorously washed five times with warm PBS to remove unbound ROSs. To determine the level of ROS internalization, an equal volume of 0.4% trypan blue was added to the PBS for 10 minutes to quench extracellular fluorescence. Trypan blue was aspirated, and 40 μl of PBS was added to the well to prevent the cells from drying out. The internalized ROSs were then documented in fluorescence photomicrographs. Fluorescence intensity was quantified by pixel densitometry using ImageJ software (National Institutes of Health, Bethesda, Md.) for photomicrograph analysis. Photomicrographs from three wells for each condition were averaged within each assay. Separate experiments were normalized to the positive control ARPE-19 cell line, which was assayed in each experiment.

Results

Nicotinamide Speeds Up Early Eye Field Differentiation. Because nicotinamide had previously been shown to increase differentiation of RPE from pluripotent stem cells in Idelson M, Alper R, Obolensky A et al. Directed differentiation of human embryonic stem cells into functional retinal pigment epithelium cells. Cell Stem Cell 2009; 5:396-408, it was tested whether nicotinamide would influence differentiation at early stages of eye field development. In this first segment of differentiation, cell clumps are mechanically dissected from pluripotent stem cell colonies and seeded on Matrigel in the presence of IGF1, Noggin, and DKK1. On day 2, bFGF is added. The addition of nicotinamide to IGF1, Noggin, Dkk1, and bFGF significantly decreased expression of the pluripotency genes Oct4 and Nanog on day 4 compared with controls. Expression of early neural/early eye field markers Lhx2 and Rax increased in the presence of nicotinamide on day 4 compared with controls; however, the increase in Rax was not significant. Interestingly, Pax6(-5a) expression was similar between nicotinamide and control conditions. Cells in the presence of nicotinamide rapidly adopted a radial/rosette morphology compared with control cells, which still contained a large percentage of cells with undifferentiated morphology. Control cells expanded more rapidly than cells in nicotinamide.

Nicotinamide can have many effects on cultured cells, including inhibition of poly(ADP-ribose) polymerase (PARP), which can protect cells from oxidative stress. To examine the mechanism of nicotinamide induced differentiation, the ability of 3-aminobenzamide, an inhibitor of PARP, to recapitulate the effects of nicotinamide was tested. 3-Aminobenzamide reduced levels of Oct4 and Nanog compared with controls on day 4, but not as much as nicotinamide. Similarly, 3-aminobenz-amide significantly increased levels of Lhx2 and Rax compared with controls on day 4, but not as much as nicotinamide. Overall, 3-aminobenzamide was able to partially recapitulate the effects of nicotinamide.

Activin A, SU5402, and VIP Direct Early Eye Field Cells to an RPE Fate. Following the acquisition of early eye field markers by day 4 (FIG. 1B), it was sought to direct the cell to RPE instead of neural retina. With this in mind, the addition of nicotinamide (added days 0-4) was phased out, Noggin (added days 0-4), bFGF (added days 2-4), IGF1 (added days 0-6), and Dkk1 (added days 0-6) and tested the effect of Activin A, SU5402, and VIP on RPE specification.

The addition of Activin A on days 4-10 had little effect on gene expression of Mitf, a marker of the optic vesicle and of RPE. Expression of Rax, a marker of the early eye field and neural retina, was significantly decreased. Addition of SU5402 on days 6-10 had little effect on expression of either Mitf or Rax; however, in combination with Activin A, expression of Rax was further decreased. VIP has been previously shown to speed up maturation of cultured primary RPE by increasing intracellular cAMP and activating pp60(c-src), as described in Koh S M. VIP enhances the differentiation of retinal pigment epithelium in culture: From cAMP and pp60(c-src) to melanogenesis and development of fluid transport capacity. Prog Retin Eye Res 2000; 19:669-688. Addition of VIP on days 6-10 significantly increased expression of RPE marker genes Mitf, tyrosinase, and PEDF. Consistent with the roles of Mitf and tyrosinase in pigment synthesis, pigmentation was increased in cultures containing VIP between days 10 and 14. By day 10, sheets of cells with cobblestone morphology and distinct borders were visible.

Differentiation to RPE Is Highly Efficient. Following 4 more days in culture with Activin A, SU5402, and VIP, the borders of cobblestone sheets became more defined, and some cells began to pigment Immunocytochemistry for the melanosomal protein Pme117 (upon which melanin pigment is deposited) exclusively labeled these pigmenting sheets of cells. Quantitative polymerase chain reaction (qPCR) analysis showed that compared with cells differentiated in B27/N2 containing basal medium only (no factor differentiation), cells that had been exposed to RPE differentiation factors (nicotinamide, IGF1, DKK1, Noggin, bFGF, Activin A, SU5402, and VIP) had significantly increased levels of the RPE marker genes Mitf, Tyrosinase, Tyrp2, PEDF, BEST1, and Pme117. Additional immunocytochemistry revealed Mitf expression exclusively in pigmenting sheets of cells, whereas Lhx2 and ZO1 could be found in both pigmenting sheets and non-RPE cells. Interestingly, in addition to Lhx2, some non-RPE cells expressed Oct4. When isolated and replated in pluripotent stem cell conditions, these cells did not form colonies with typical undifferentiated stem cell morphology, and many appeared to differentiate into neurons.

To determine the efficiency of differentiation, flow cytometry was performed using the Pme117 antibody, which is highly sensitive and which labels only pigmenting sheets of cells by immunocytochemistry. Also examined was the loss of the pluripotency marker Oct4 by flow cytometry. It was found that H9 cells could be differentiated into Pme117$^+$ cells by day 14 with an average efficiency of 78.5% (±1.2%, n=6, H9-RPE). This was highly significant when compared with either undifferentiated H9 cells (12.8%±2.4%, n=3, H9) or cells differentiated in basal medium alone (25.2%±1.6%, n=3, no factor differentiation). The differentiation protocol was tested on two additional pluripotent stem cell lines: the embryonic stem cell line UCSF4 and the induced pluripotent stem cell line IMR904. The UCSF4 line yielded Pme117$^+$ cells with an efficiency similar to H9 cells (79.8%±0.88%, n=3, UCSF4-RPE), whereas the IMR904 line was slightly less efficient (63%±0.88%, n=3, IMR904-RPE). The percentage of Oct4$^+$ cells was less than 5% in all conditions except undifferentiated H9 cells (98.1%±0.6%, n=3, H9).

Examination of representative flow cytometry histograms reveals population expression levels of Pme117 and Oct4 protein on day 14. H9-RPE cells differentiated in basal media (no factor differentiation), undifferentiated H9 cells, the melanocyte cell line MeWo (a positive control for Pme117), and the fibroblast line Hs27 (a negative control for both Oct4 and Pme117) were compared. Interestingly, undifferentiated H9 cells appeared to express low levels of Pme117. This is consistent with findings in our own lab and others that undifferentiated stem cells express low levels of this transcript. A high level of Pme117 protein expression was only seen in H9-RPE cells and the positive control MeWo cells (melanocytes).

Interestingly, cells left in culture past day 14 with Activin A, SU5402, and VIP led to death of non-RPE cells. This suggests that the culture conditions are both directive and selective for RPE. Because one of the goals was to determine the earliest time that homogenous cultures of RPE could be generated, day 14 as the end point of directed differentiation was focused on.

Protein and mRNA Time Courses Reveal Stages of RPE Development. To better understand the nature of our differentiation protocol, both protein and mRNA expression of a panel of genes over 14 days of differentiation were analyzed. As expected, pluripotency gene and protein expression (Oct4 and Nanog) decreased rapidly over the first 4 days. Interestingly, Oct4 and Nanog expression increased slightly between days 4 and 6, during which time Activin A was added to the protocol. Early neural and eye field markers (Lhx2, Pax6(−5a), Pax6(+5a), and Rax) were expressed as early as day 2, with expression increasing throughout the 14-day time period with the exception of Rax. Rax expression was transient, increasing from days 2-6 and then rapidly decreasing between days 6 and 8. At day 6, IGF1 and DKK1 were removed from the protocol, whereas SU5402 and VIP were added, which could account for the decrease in Rax expression. RPE marker genes were expressed slightly later in two phases, between days 4 and 6 (Mitf, PEDF, and BEST1) and between days 6 and 8 (Pme117, Tyrosinase, and Tyrp2). Interestingly, Otx2 mRNA and protein were expressed at relatively consistent levels throughout differentiation.

Differentiated Cells Can Be Enriched on Day 14 to Homogenous Cultures of Functional RPE. To generate more homogenous populations of RPE, readily visible sheets on day 14 were mechanically isolated, dissociated into single cells, and replated in an RPE medium described in Buchholz D E, Hikita S T, Rowland T J et al. Derivation of functional retinal pigmented epithelium from induced pluripotent stem cells. STEM CELLS 2009; 27:2427-2434, on Matrigel-coated tissue culture plastic, chambered slides, or Transwell inserts. Surprisingly, RPE enriched on day 14 were sensitive to singe-cell dissociation in the media tested, leading to cell death or senescence. Because the Rho-associated protein kinase (ROCK) inhibitor Y27632 has been previously shown to support single-cell dissociation of epithelial cells, including pluripotent stem cells, the ability of this small molecule to rescue dissociated RPE was tested. The addition of Y27632 at 10 μM for the first 3 days after passage facilitated RPE survival and maturation.

After enriching RPE at day 14, the cells were allowed to redifferentiate for 30 days and then analyzed gene and protein expression and phagocytosis of rod outer segments. To analyze gene expression, hESC-RPE, cultured fetal human RPE (fRPE), and Hs27 fibroblasts were cultured on Transwell inserts for 30 days. qPCR analysis showed similar levels of expression of all RPE marker genes between hESC-RPE and fRPE. Hs27 cells were used as a negative control for RPE-specific genes; however, some Mitf, PEDF, and BEST1 expression in Hs27 was detected. Compared with undifferentiated H9 cells, expression of Oct4 was ~1,000-fold lower in all other cell lines.

Immunocytochemistry of cells enriched at day 14 and grown on chambered slides for 30 days showed homogenous populations of RPE based on Mitf, Otx2, Lhx2, ZO1, and Pme117 expression. Expression of BEST1 and RPE65, markers of more mature RPE, was heterogeneous, indicating varying levels of maturity in these cultures. Integrin αv was localized apically compared with Otx2 nuclear expression, showing proper polarized protein trafficking in these cells (FIG. 4B, inset in Integrin αv/Otx2 panel). Although some Oct4$^+$ cells were present at day 14 of initial differentiation, no Oct4$^+$ cells were observed following enrichment and 30 days of culture.

To determine whether these hESC-RPE were functional, their ability to carry out phagocytosis of fluorescently labeled ROSs was tested. Compared with the negative control Hs27 cells, hESC-RPE internalized significantly more ROSs. This internalization was blocked by an antibody against integrin αvβ5, showing that both hESC-RPE and fRPE use the same receptor for ROS phagocytosis. hESC-RPE ROS phagocytosis was even greater than that of fRPE, although both RPE lines internalized significantly more ROSs than Hs27 cells.

Discussion

These results demonstrate the generation of high quality RPE cells within 14 days, with high yields.

Nicotinamide has previously been used to differentiate pluripotent stem cells into RPE. It was shown that nicotinamide had an antiapoptotic effect following 2 weeks of differentiation, in line with other studies showing neural protection by nicotinamide. Based on previous research, it was suggested that this action could be through inhibition of poly(ADP-ribose) polymerase-1 (PARP1), which was found to regulate cell death upon hESC neural induction. In these experiments, the addition of nicotinamide to retinal inducing factors IGF1, DKK1, Noggin, and bFGF decreased expression of pluripotency genes while concomitantly increasing neural/early eye field genes by day 4. Because it is known that the IGF1, DKK1, Noggin, and bFGF protocol induces expression of Lhx2, Rax, and Pax6, these gene expression changes suggest that the addition of nicotinamide speeds up differentiation. Interestingly, not all neural/early eye field genes were affected by nicotinamide. Although Lhx2 and Rax expression increased with nicotinamide addition on day 4, Pax6 expression was slightly lower, although this change was not significant. This suggests that nicotinamide may not have an effect on Pax6 and may act on a factor downstream.

Fewer cells were seen in nicotinamide conditions, which could result from either cell death or a decrease in proliferation. A decrease in proliferation has previously been reported upon exposure of hESCs to nicotinamide. Although these results suggest a role for nicotinamide outside of cell survival, the role of PARP1 inhibition was tested. To test the role of PARP1 inhibition in the nicotinamide induced differentiation, the ability of another PARP1 inhibitor, 3-aminobenzamide, to induce differentiation was tested. It was observed that 3-aminobenzamide could partially recapitulate the effects seen with nicotinamide.

Although the exact mechanism of nicotinamide-induced neuronal differentiation remains to be elucidated, it is clear that nicotinamide can potentiate differentiation, and this potentiation appears to act at least partially through PARP inhibition. Neuroprotective/antiapoptotic effects of PARP inhibition may also play a role. It was observed that Nicotinamide was found to be a useful tool to speed up initial neural differentiation and could potentially be applied to other neural differentiation protocols.

The addition of Activin A and the FGFR1 inhibitor SU5402 led to only slight increases in RPE genes, whereas the early eye field/neural retina marker Rax was significantly downregulated by day 10. The former may be attributed to the potent retinal inducing properties of IGF1, whereas the latter confirms the roles of Activin A and FGF signaling in the optic vesicle to optic cup stages of eye development. This is seen in both animal and hESC models where Activin signaling and FGF inhibition direct the progenitor cells toward RPE (Rax$^-$) instead of neural retina (Rax$^+$). The addition of VIP significantly increases expression of Mitf, Tyrosinase, and PEDF, in agreement with results found in primary cultures of RPE. VIP caused an increase in pigmentation at earlier time points.

By day 14 of differentiation, sheets of RPE can clearly be seen with defined borders that express several RPE marker genes and proteins. By this time cells have begun to pigment. Interestingly, the speed of pigmentation appears to be inversely correlated with the efficiency of RPE differentiation or size of the RPE sheet. Small sheets (<500 μm) tended to pigment faster than large sheets (>5 mm) This suggests that signals coming from non-RPE cells may have a positive effect on pigmentation.

Generation of RPE from both H9 and UCSF4 embryonic stem cell lines was highly efficient, averaging close to 80% based on Pme117 immunoreactivity. This method induced efficient differentiation of RPE in the UCSF4 cell line, which is resistant to RPE differentiation using the spontaneous method. The efficiency of RPE generation from IMR904 induced pluripotent stem (iPS) cells was somewhat less efficient at 60%.

Cells that did not express Pme117 on day 14 of differentiation expressed Oct4 and Lhx2. When isolated on day 14 and placed back in embryonic stem cell conditions, these cells did not form colonies that resembled embryonic stem cell morphology, and many appeared to differentiate into neurons. It appears that these cells may be stuck in a partially differentiated state. If differentiating cultures were kept longer than 14 days, these non-RPE cells began to die. Therefore, it is considered that the Activin A-, SU5402-, and VIP-supplemented medium to both direct differentiation and select for RPE over non-RPE cells, leading to virtually homogenous populations of RPE after 3 weeks.

Analysis of gene and protein expression throughout the 14-day differentiation period revealed several interesting trends. First, as expected, early neural and eye field genes were expressed first, followed by later markers of the optic vesicle and RPE. Interestingly, although gene expression followed the known developmental sequence, transition from early eye field to optic vesicle and RPE was quite rapid. This suggests that during normal development, the ability of a cell to respond to developmental cues can precede those signals by a significant amount of time, perhaps to allow time for tissue growth. Between days 4 and 6, a slight increase in Oct4 and Nanog gene expression was observed. This is likely because of the addition of Activin A on day 4 because Activin A signaling has been shown to maintain pluripotency. Consistent with recent observations in Rax-GFP pluripotent stem cells undergoing ocular morphogenesis, transient expression of Rax between days 2 and 8 was seen. This would appear to correspond with expression in the early eye field followed by downregulation in the RPE. Interestingly, Otx2, which has been shown to be repressed by Rax specifically in the early eye field of *Xenopus*, maintained a fairly consistent level of both mRNA and protein expression over the 14-day time course. In fact, Otx2 mRNA expression increased when Rax mRNA expression was at its highest. These observations, along with results from other hESC retinal differentiation protocols, suggest that Otx2 is expressed in the early eye field of humans. Alternatively, there are two known protein isoforms of Otx2 in humans and several different transcripts, which may be alternatively regulated. These experiments do not differentiate between these isoforms. There is also the possibility that maintained Otx2 expression throughout ocular differentiation may be an artifact of cell culture and may not be found in vivo.

Because morphologically distinct sheets of RPE became visible between days 10 and 14, and with the addition of the ROCK inhibitor Y27632 over the first few days of culture, RPE could be enriched at both of these time points and would mature into functional RPE when replated. However, the borders of RPE sheets at day 10 were harder to distinguish. Tight junctions among non-RPE cells made them easy to remove as sheets by dragging a pipette tip along borders with RPE.

ROCK inhibition has been used successfully to maintain survival of hESCs dissociated into single cells as well as to enhance proliferation of certain epithelial cell types. The mechanism of ROCK inhibition has been worked out in hESCs, where ROCK mediates E-cadherin cell adhesion sensing. Primary RPE cultures, when dissociated into single cells over several passages, lose their ability to redifferentiate into mature RPE and become fibroblastic in morphology. This may be a wound response for an epithelium that does not normally exist as single cells and may be similar to the effect seen following single-cell dissociation on day 14 of differentiation. Although the mechanism is not known, enrichment of RPE cells on day 14 in the presence of ROCK inhibitor can generate homogenous populations that express RPE marker genes at similar levels to cultured fetal human RPE, express proper RPE proteins, are polarized, and display integrin $\alpha v\beta 5$-dependent phagocytosis of rod outer segments.

All patents, patent applications, and publications cited in this specification are herein incorporated by reference in their entirety. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of differentiating mammalian pluripotent stem cells into retinal pigmented epithelium cells, comprising culturing pluripotent stem cells in a first medium comprising a basal medium supplemented with IGF1, DKK1, and noggin;

subsequently, culturing the cells in a second medium comprising a basal medium supplemented with IGF1, DKK1, noggin, and BFGF;

subsequently, culturing the cells in a third medium comprising a basal medium supplemented with IGF1, DKK1 and Activin A; and subsequently, culturing the cells in a fourth medium comprising a basal medium supplemented with Activin A and SU5402, thereby obtaining retinal pigmented epithelium cells.

2. The method of claim 1, wherein
the basal medium is selected from a group consisting of:
Dulbecco's Modified Eagle Medium mammalian cell culture medium, Ham's F12 medium, a 1:1 mixture of Dulbecco's Modified Eagle Medium mammalian cell culture medium and F12, Iscove's Modified Dulbecco's Medium, Neurobasal™ medium, X-Vivo™ 10 medium, Minimum Essential Medium Eagle medium, Roswell Park Memorial Institute Medium 1640, and MCDB medium.

3. The method of claim 1, wherein
noggin is present in the first medium and the second medium at a concentration between 1 and 100 ng/ml;
IGF1 is present in the first medium, the second medium, and the third medium at a concentration between 1 and 100 ng/ml;
DKK1 is present in the first medium, the second medium, and the third medium at a concentration between 1 and 50 ng/ml;
BFGF is present in the second medium at a concentration between 1 and 20 ng/ml;
Activin A is present in the third medium and the fourth medium at a concentration between 10 and 200 ng/ml; and
SU5402 is present in the fourth medium at a concentration between 1 and 100 µM.

4. The method of claim 1, wherein
nicotinamide is present in the first medium, the second medium, or both the first and second media.

5. The method of claim 4, wherein
nicotinamide is present at a concentration between 1 and 100 mM.

6. The method of claim 1, wherein
VIP is present in the fourth medium.

7. The method of claim 6, wherein
VIP is present at a concentration between 0.1 to 100 µM.

8. The method of claim 1, wherein
the transition between the first and second medium is made 24-72 hours after the initiation of culture in the first medium.

9. The method of claim 1, wherein
the transition between the second and third medium is made 48-144 hours after the initiation of culture in the first medium.

10. The method of claim 1, wherein
the transition between the third and fourth medium is made 60 to 192 hours after the initiation of culture in the first medium.

* * * * *